United States Patent
Neumann et al.

(10) Patent No.: US 10,496,729 B2
(45) Date of Patent: Dec. 3, 2019

(54) METHOD AND SYSTEM FOR IMAGE-BASED ESTIMATION OF MULTI-PHYSICS PARAMETERS AND THEIR UNCERTAINTY FOR PATIENT-SPECIFIC SIMULATION OF ORGAN FUNCTION

(71) Applicant: Siemens Healthcare GmbH, Erlangen (DE)

(72) Inventors: Dominik Neumann, Erlangen (DE); Tommaso Mansi, Plainsboro, NJ (US); Bogdan Georgescu, Plainsboro, NJ (US); Ali Kamen, Skillman, NJ (US); Dorin Comaniciu, Princeton Junction, NJ (US)

(*) Notice: Subject to any disclaimer, the term of this patent is extended or adjusted under 35 U.S.C. 154(b) by 389 days.

(21) Appl. No.: 14/630,075

(22) Filed: Feb. 24, 2015

(65) Prior Publication Data
US 2015/0242589 A1    Aug. 27, 2015

Related U.S. Application Data

(60) Provisional application No. 61/944,093, filed on Feb. 25, 2014.

(51) Int. Cl.
*G06F 17/18*    (2006.01)
*G06N 7/00*    (2006.01)

(52) U.S. Cl.
CPC ........ *G06F 17/18* (2013.01); *A61B 2576/023* (2013.01); *G06N 7/005* (2013.01)

(58) Field of Classification Search
CPC ... G06F 19/3437; G06F 17/18; G06T 7/0012; A61B 90/37; A61B 6/504; A61B 2034/105; A61B 2576/023; G06N 7/005
See application file for complete search history.

(56) References Cited

U.S. PATENT DOCUMENTS

7,462,153 B2 * 12/2008 Bostian ............... G06F 19/3437
                                              600/508
7,706,610 B2 *  4/2010 Zhang ..................... G06K 9/38
                                              382/173
(Continued)

FOREIGN PATENT DOCUMENTS

WO    2014113746 A1    7/2014
WO    2015031576 A1    3/2015

OTHER PUBLICATIONS

Fei-Fei Li, Lecture 13: k-means and mean-shift clustering, Oct. 27, 2013, Stanford Vision Lab.*
(Continued)

*Primary Examiner* — Rehana Perveen
*Assistant Examiner* — Chuen-Meei Gan

(57) ABSTRACT

A method and system for estimating tissue parameters of a computational model of organ function and their uncertainty due to model assumptions, data noise and optimization limitations is disclosed. As applied to a cardiac use-case, a patient-specific anatomical heart model is generated from medical image data of a patient. A patient-specific computational heart model is generated based on the patient-specific anatomical heart model. Patient-specific parameters and corresponding uncertainty values are estimated for at least a subset of parameters of the patient-specific computational heart model. A surrogate model is estimated for a forward model of cardiac function, and the surrogate model is applied within Bayesian inference to estimate the posterior probability density function of the parameter space of the forward model. Cardiac function for the patient is simulated using the patient-specific computational heart model. The estimated parameters, their uncertainty, and the computed cardiac function are displayed to the user.

51 Claims, 8 Drawing Sheets

(56) References Cited

U.S. PATENT DOCUMENTS

| | | | |
|---|---|---|---|
| 8,098,918 B2 | 1/2012 | Zheng et al. | |
| 8,157,742 B2* | 4/2012 | Taylor | A61B 5/02007 600/481 |
| 8,386,188 B2 | 2/2013 | Taylor et al. | |
| 8,824,752 B1* | 9/2014 | Fonte | G06T 7/0012 382/126 |
| 2003/0095121 A1* | 5/2003 | Huseyin | G06T 7/0012 345/423 |
| 2003/0197704 A1* | 10/2003 | Tek | G06T 17/00 345/474 |
| 2005/0004833 A1* | 1/2005 | McRae | G05B 17/02 703/2 |
| 2007/0172105 A1* | 7/2007 | Bahlmann | G06K 9/00 382/131 |
| 2007/0242901 A1* | 10/2007 | Huang | G06K 9/4671 382/294 |
| 2010/0040272 A1 | 2/2010 | Zheng et al. | |
| 2010/0042563 A1* | 2/2010 | Livingston | G06K 9/6226 706/12 |
| 2012/0022843 A1* | 1/2012 | Ionasec | G06T 13/20 703/9 |
| 2012/0041301 A1 | 2/2012 | Redel | |
| 2012/0041318 A1* | 2/2012 | Taylor | A61B 5/02007 600/504 |
| 2012/0072190 A1 | 3/2012 | Sharma et al. | |
| 2012/0121151 A1 | 5/2012 | Bernhardt et al. | |
| 2012/0203530 A1 | 8/2012 | Sharma et al. | |
| 2012/0215512 A1* | 8/2012 | Sarma | E21B 43/00 703/10 |
| 2012/0239174 A1* | 9/2012 | Shotton | G06K 9/00362 700/93 |
| 2013/0197881 A1 | 8/2013 | Mansi et al. | |
| 2013/0197884 A1 | 8/2013 | Mansi et al. | |
| 2013/0226542 A1 | 8/2013 | Rapaka et al. | |
| 2015/0042646 A1 | 2/2015 | Comaniciu et al. | |
| 2016/0196384 A1* | 7/2016 | Mansi | G06F 19/321 600/301 |

OTHER PUBLICATIONS

Konukoglu et al, Efficient probabilistic model personalization integrating uncertainty on data and parameters: Application to Eikonal-Diffusion models in cardiac electrophysiology, Progress in Biophysical and Molecular Biology 107 (2011) 134-146. Jul. 7, 2011.*
Okada et al, Robust Anisotropic Gaussian Fitting for Volumetric Characterization of Pulmonary Nodules in Multislice CT, IEEE Transactions on Medical Imaging, vol. 24 No. 3 Mar. 2005.*
Shaw et al, Mechanical Analysis of Single Myocyte Contraction in a 3-D Elastic Matrix, PLOS ONE, vol. 8 issue 10 p. 1-13. Oct. 2013.*
Dominik Neumann et al, A self-taught artificial agent for multiphysics computational model personalization, Medical Image Analysis 34 (2016) 52-64 (Year: 2016).*
Yang Wang, Bogdan Georgescu, Terrence Chen, Wen Wu, Peng Wang, Xiaoguang Lu, Razvan Ionasec, Yefeng Zheng and Dorin Comaniciu, Learning-Based Detection and Tracking in Medical Imaging: A Probabilistic Approach, Deformation Models, Lecture Notes in Computational Vision and Biomechanics (Year: 2013).*
Adarsh Krishnamurthy et al, Patient-Specific Models of Cardiac Biomechanics, J Comput Phys. Jul. 1, 2013; 244: 4-21. (Year: 2013 ).*
Mikael Wallman et al, Computational methods to reduce uncertainty in the estimation of cardiac conduction properties from electroanatomical recordings, Medical Image Analysis 18 (2014) 228-240 (Year: 2013).*
Dikici et al., "Quantification of Delayed Enhancement MR Images", In Proc. MICCAI 2004, LNCS 3216, pp. 250-257, 2004.

Peyrat et al., "A Computational Framework for the Statistical Analysis of Cardiac Diffusion Tensors: Application to a Small Database of Canine Hearts", IEEE TMI, 26(11): 1500-1514, 2007.
Mitchell et al., "A Two-Current Model for the Dynamics of Cardiac Membrane", Bulletin of Mathematical Biology, 65(5):767-793, 2003.
Powell, "Developments of NEWUOA for Minimization Without Derivatives", J. Num. Analysis, 2008.
McMurray et al., "ESC Guidelines for the Diagnosis and Treatment of Acute and Chronic Heart Failure 2012", European Journal of Heart Failure, pp. 803-869.
Trayanova, Natalia A., "Whole-Heart Modeling Applications to Cardiac Electrophysiology and Electromechanics", Circulation Research, 2011, 21 pgs.
Prakosa et al., "Cardiac Electrophysiological Activation Pattern Estimation From Images Using a Patient-Specific Database of Synthetic Image Sequences", IEEE Transactions on Biomedical Engineering, vol. 61, No. 2, Feb. 2014, pp. 235-245.
Wong et al., "Velocity-Based Cardiac Contractility Personalization from Images Using Derivative-Free Optimization", Journal of the Mechanical Behavior of Biomedical Materials, Dec. 2013, 19 pgs.
Le Folgoc et al., "Current-Based 4D Shape Analysis for the Mechanical Personalization of Heart Models", MCV—MICCAI Workshop on Medical Computer Vision, 2012, 10 pgs.
Adams et al., "Dakota, A Multilevel Parallel Object-Oriented Framework for Design Optimization, Parameter Estimation, Uncertainty Quantification, and Sensitivity Analysis", Version 5.4 Developers Manual, SAND2010-2185, Nov. 7, 2013, 1047 pgs.
Powell, M.J.D., "The BOBYQA Algorithm for Bound Constrained Optimization without Derivatives", Cambridge NA Report NA2009-06, University of Cambridge, Department of Applied Mathematics and Theoretical Physics, 2009, 39 pgs.
Chabiniok et al., "Estimation of Tissue Contractility from Cardiac Cine-MRI Using a Biomechanical Heart Model", Biomechanics and Modeling in Mechanobiology 11, Dec. 22, 2011, 33 pgs.
Xi et al., "Myocardial Transversely Isotropic Material Parameter Estimation from In-Silico Measurements Based on a Reduced-Order Unscented Kalman Filter", Journal of the Mechanical Behavior of Biomedical Materials, Oct. 2011, pp. 1090-1102.
Delingette et al., "Personalization of Cardiac Motion and Contractility from Images using Variational Data Assimilation", IEEE Transactions on Biomedical Engineering, Jun. 2011, 5 pgs.
Zheng et al., "Four-Chamber Heart Modeling and Automatic Segmentation for 3D Cardiac CT Volumes Using Marginal Space Learning and Steerable Features", IEEE Transactions on Medical Imaging, 2008, 14 pgs.
Zettinig et al., "From Medical Images to Fast Computational Models of Heart Electromechanics: An Integrated Framework towards Clinical Use", Functioning Imaging and Modeling of the Heart, 2013, Springer, 9 pgs.
Rapaka et al., "LBM-EP: Lattice-Boltzmann Method for Fast Cardiac Electrophysiology Simulation from 3D Images", MICCAI 2012, Part II, LNCS 7511, Springer-Verlag Berlin Heidelberg, pp. 33-40.
Sermesant et al., "An Electromechanical Model of the Heart for Image Analysis and Simulation", IEEE Transactions on Medical Imaging, vol. 25, No. 5, May 2006, pp. 612-625.
Zettinig et al., "Fast Data-Driven Calibration of a Cardiac Electrophysiology Model from Images and ECG", MICCAI Sep. 2013, 8 pgs.
Tarantola, Albert, "Inverse Problem Theory and Methods for Model Parameter Estimation", SIAM, 2004, 42 pgs.
Marzouk et al., "Stochastic Spectral Methods for Efficient Bayesian Solution of Inverse Problems", Journal of computational Physics, 2006; pp. 560-586.
Haario et al., "DRAM: Efficient Adaptive MCMC", Statistics and Computing, 2006 Springer, 17 pgs.

* cited by examiner

METHOD AND SYSTEM FOR IMAGE-BASED ESTIMATION OF MULTI-PHYSICS PARAMETERS AND THEIR UNCERTAINTY FOR PATIENT-SPECIFIC SIMULATION OF ORGAN FUNCTION

This application claims the benefit of U.S. Provisional Application No. 61/944,093, filed Feb. 25, 2014, the disclosure of which is herein incorporated by reference.

BACKGROUND OF THE INVENTION

The present invention relates to personalization of computational models of human organs, such as the heart, and more particularly, to estimation of patient-specific model parameters and their uncertainty given noise in the data, model assumptions and estimation limitations.

Computational models have been recently explored for various human organs. For example, a motivation for the use of cardiac modeling relates to management of cardiomyopathy, one of the most common types of cardiovascular disease with significant mortality and morbidity rates. Cardiomyopathy is among the main causes of heart failure in developed countries. Clinical management of cardiomyopathy patients is challenging due to the wide variety of disease etiology and therapy options. Computational heart models are being explored as tools to improve patient stratification, risk prediction, therapy planning, guidance and follow-up. However, the high level of model complexity, their unavoidable simplifying assumptions and the limited availability of often noisy measurements hinder the personalization of these models that is necessary for such computational heart models to be clinically useful.

BRIEF SUMMARY OF THE INVENTION

The present invention provides a method and system for the estimation of the parameters of computational models of organ function from medical images and clinical data, along with their uncertainty due to model assumptions, data noise and optimization limitations. Embodiments of the present invention are illustrated herein on the use case of cardiac modeling, and more specifically on cardiac biomechanics. However, embodiments of the present invention can also be applied to other cardiac physics (e.g. electrophysiology, hemodynamics), as well as other organ models (e.g. lung motion, heat conduction in tissues). Embodiments of the present invention utilize a stochastic method to estimate patient-specific parameters and their uncertainty due to noise in measurements used to personalize the model. To make the problem computationally tractable, embodiments of the present invention estimate a surrogate model of the computational model under consideration (e.g. cardiac biomechanics), for instance using polynomial chaos expansion like in the presented embodiment, and apply the surrogate model with Bayesian inference to estimate the posterior probability density of the model parameters knowing the noisy measurements. Embodiments of the present invention then utilize the mean-shift algorithm to automatically find the modes of the posterior probability function and select the most likely mode while being robust to noise. The center of the mode corresponds to the estimated model parameters, and the local width of the mode their uncertainty.

In one embodiment of the present invention, a surrogate model is estimated for a computational model of organ function. A plurality of forward model responses for the computational model of organ function corresponding to a plurality of parameter values for tissue parameters of the computational model of organ function are estimated using the surrogate model. For each of a plurality of noise levels, a respective set of samples of a posterior density of a parameter space of the tissue parameters of the computational model of organ function is generated based on the plurality of forward model responses estimated using the surrogate model. A number of modes is determined for each respective set of samples. A respective Gaussian mixture model (GMM) is fitted to each respective set of samples based on the number of modes determined for each respective set of samples, resulting in a plurality of GMM's in which each GMM corresponds to one of the plurality of noise levels. A most likely point in the plurality of GMMs is selected as an estimate of the patient-specific tissue parameters of the computational model of organ function, and a confidence region for the estimate of the patient-specific tissue parameters is determined based on the plurality of GMMs.

In another embodiment of the present invention, focusing on a cardiac application, a patient-specific anatomical heart model is generated from medical image data of a patient. A patient-specific computational heart model is generated based on the patient-specific anatomical heart model and patient-specific clinical data, and generating the patient-specific computational heart model comprises estimating patient-specific parameters and corresponding uncertainty values for at least a subset of parameters of the patient-specific computational heart model. Cardiac function for the patient is simulated using the patient-specific computational heart model These and other advantages of the invention will be apparent to those of ordinary skill in the art by reference to the following detailed description and the accompanying drawings.

DETAILED DESCRIPTION

The present invention relates to the estimation of patient-specific parameters of computational models of organ function from medical images and clinical data, along with their uncertainty due to model assumptions, data noise and inverse problem algorithm limitations. The invention is illustrated on the specific use-case of the estimation of cardiac tissue biomechanical properties from medical images and clinical data, although it could be applied to other physics (e.g. electrophysiology, cardiac hemodynamics) and other organs (e.g. lung motion, liver heat capacity). A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system, or available through a network system.

Clinical applications of computational cardiac models require precise personalization. Various techniques have been proposed to solve the inverse problem of cardiac modeling, i.e., the estimation of model parameters from clinical data for patient-specific computations. Solutions involving non-linear least squares (NLS) solvers incorporating specialized cost functions which can be strictly tailored to a particular problem are often used due to the high availability of easy to use general purpose frameworks. However, due to parameter non-observability, limited data, uncertainty in clinical measurements, and modeling assumptions, various combinations of parameters values can exist that yield the same apparent goodness of fit. Accordingly, there is a need for quantifying the uncertainty of the estimated parameters, as well as a need to ascertain the uniqueness of an estimated solution.

Embodiments of the present invention utilize a stochastic method to estimate patient-specific parameters for a computational heart model and their uncertainty due to noise in measurements used to personalize the model. While the forward model could be employed directly, should it be fast enough to compute, embodiments of the present invention utilize polynomial chaos expansion to estimate a surrogate for a model of cardiac function to make the problem computationally tractable. The surrogate model, or the forward model, is then applied with Bayesian inference to estimate posterior probabilities for different model parameter values. Embodiments of the present invention then utilize a strategy based on the mean-shift algorithm to find the optimal parameter values by exploring the space of measurement uncertainties.

Figure 1:
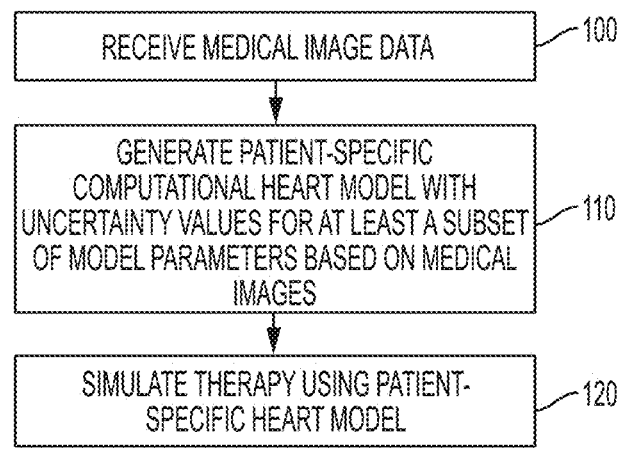
FIG. 1 illustrates a method for patient-specific cardiac simulation according to an embodiment of the present invention.

FIG. 1 illustrates a method for patient-specific cardiac simulation according to an embodiment of the present invention. It is to be understood, that although FIG. 1 illustrates an example in which estimation of patient-specific model parameters and their uncertainties is applied to a computational heart model, the present invention is not limited thereto, and the framework for estimating the model parameters and their uncertainties can be similarly applied to computational models for other organs (e.g., lung motion, liver heat capacity), as well. As illustrated in FIG. 1, at step 100 clinical data and medical images of a patient are received. The clinical data can include electrophysiology data such as electrocardiogram (ECG) and/or pressure data such as invasive catheter measurements or pressure cuff measurements. The medical images may be a sequence of 3D medical images acquired over at least one complete heart cycle. In advantageous embodiments of the present invention, the medical images can be magnetic resonance imaging (MRI) images, computer tomography (CT) images and/or ultrasound images, but the present invention is not necessarily limited to these imaging modalities. The medical images may be received directly from a medical imaging device, such as a magnetic resonance (MR), CT or ultrasound scanner, or the medical images may be received by loading stored medical images of a patient.

At step 110, a patient-specific computational heart model is generated based on the medical images and the clinical data of the patient. The patient-specific computational heart model is generated using an inverse problem to adjust parameters of the computational heart model such that simulated parameters, such as heart motion, ejection fraction, etc., output by the patient-specific computational heart model match the clinical data and medical images observed for the patient. According to an advantageous embodiment, uncertainty values are calculated for at least a subset of parameters of the computational heart model. For example, parameters of a model of cardiac function included in the computational heart model, such as a cardiac electrophysiology model, a cardiac hemodynamics model, or a cardiac biomechanics model, can estimated with uncertainty values.

At step 120, cardiac function is simulated for the patient using the patient-specific computational heart model. The simulations can be used for patient-specific planning or guidance of cardiac therapies, such as cardiac resynchronization therapy (CRT), ablation therapy, surgery, etc. Simulated parameters, such as ejection fraction, ECG, and heart dynamics, are calculated based on the cardiac therapy simulations, and such simulated parameters are used as predictors of the patient response to the cardiac therapies. Various cardiac simulations can be performed for a particular cardiac therapy while varying parameters in the subset of parameters within confidence intervals determined for those parameters to evaluate various possible therapy responses due to the uncertainties in the model parameters, and to provide the user with confidence values in model predictions.

Figure 2:
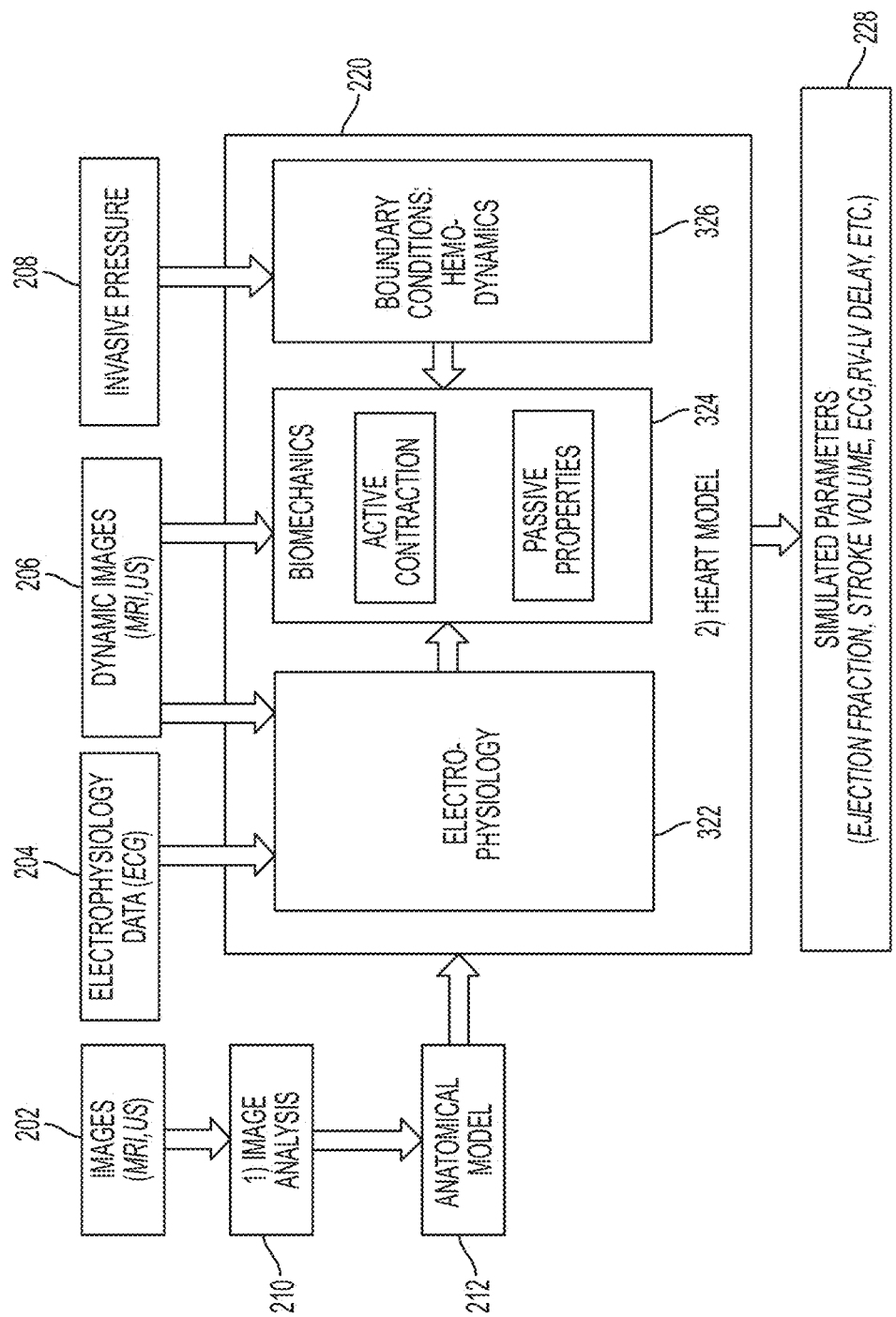
FIG. 2 illustrates a detailed framework of the computational heart model according to an embodiment of the present invention.

FIG. 2 illustrates a detailed framework of the computational heart model according to an embodiment of the present invention. As illustrated in FIG. 2, the patient-specific heart model includes four main models representing cardiac anatomy, cardiac electrophysiology, cardiac biomechanics, and cardiac hemodynamics. These models are connected as follows. Starting from a medical image 202 of the heart (MRI, CT, Ultrasound), at step 210, a detailed anatomical model 212 of the patient's heart is generated. In an exemplary embodiment, a detailed anatomical model is generated of the two ventricles only, but the present invention is not limited thereto. Arteries and atria are modeled as boundary conditions of the system. The anatomical model 212 comprises the bi-ventricular geometry, the orientation of myocyte fibers, and any information that varies spatially such as action potential duration, scars, etc. The anatomical model 212 is then given as input to the Heart Model subsystem (step 220), which will compute myocardium motion over time according to three main sub-parts: the cardiac electrophysiology model 222, the cardiac biomechanics model 224, and the cardiac hemodynamics model 226. Each of these models of cardiac function can be fitted to patient data using inverse problem approaches and all available preoperative data such as dynamic images 206, ECG 204, invasive pressure measurements 208, etc., such that the simulated parameters 230 match the clinical observations. Alternatively, these models can be fitted using the approach presented herein. Once the model is personalized, cardiac therapy, such as CRT, ablation therapy, surgery, valve planning, etc. can be simulated by pacing the model at various locations for instance. Clinical parameters are computed from the simulation to quantify the predicted patient response to the therapy. Depending on the application, the model can include of one, several or all of the above-mentioned sub-parts.

In an exemplary embodiment, in order to generate the anatomical model 212, anatomical models of the left ventricle (LV) and right ventricle (RV) are extracted from the medical images. Although it is possible to extract models for all of the heart chambers, in an advantageous embodiment, only the geometry LV and RV are explicitly modeled. If the application targets atrial anatomy, at least one of the atria can be segmented and used as computational domain. For each of the LV and the RV, the heart chamber segmentation can be formulated as a two-step learning problem: anatomical structure localization and boundary delineation. Marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. The classifiers in the lower dimensional marginal spaces are used to prune the searching space efficiently. This object localization stage results in an estimated transformation (position, orientation, and scale) of the object (e.g., heart chamber). After automatic object localization, the mean shape model of the object is aligned with the estimated transformation to get a rough estimate of the object shape. The shape is then deformed locally to fit the object boundary using an active shape model (ASM) and a machine learning based boundary detector. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference.

The patient-specific LV and RV models are then fused into a single anatomical model of the bi-ventricular myocardium. In particular, the LV and RV anatomies are fused into a single volumetric mesh representation. The LV and RV models can be fused and a volumetric mesh estimated (based on tetrahedral for instance), on which vertices are tagged into surface zones according to the underlying anatomy. According to an advantageous implementation, tetrahedral elements can be used to accurately represent the details of the bi-ventricular anatomy. Spatial information can then be mapped onto the anatomical model of the bi-ventricular myocardium. Spatial information, such as scars, grey zones, and fibrosis can be identified in images, such as late enhancement MRI. For example, the spatial information may be automatically identified using trained classifiers or may be manually identified by a clinician. The spatial information is mapped onto the tetrahedral mesh representing the bi-ventricular myocardium. This information is important to simulate the electrical wave around scars, in particular for wave-reentry assessment and correctly capture impaired cardiac mechanics due to ill-functioning or dead cells.

Figure 3:
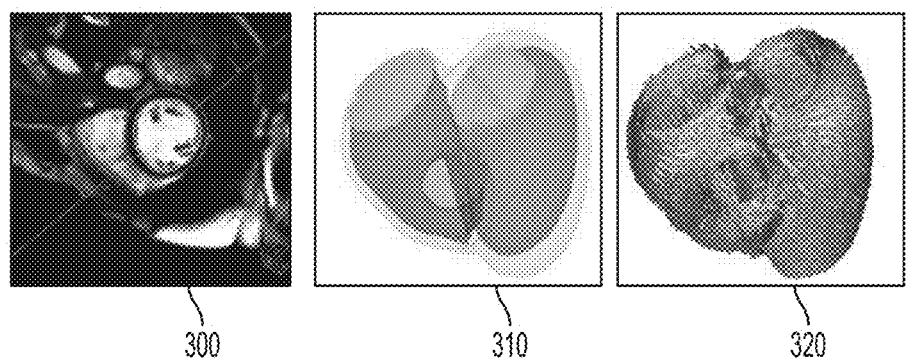
FIG. 3 illustrates exemplary results of generating a patient-specific anatomical heart model.

A model of fiber orientation can be automatically calculated based on the patient-specific geometry. In an advantageous implementation, the model of fiber orientation can be automatically calculated using a rule-based approach. A generic model of myocardium fiber architecture that includes fiber and fiber sheets is computed. A rule-based strategy is followed to generate the fiber architecture to cover the entire bi-ventricular myocardium from apex to valves. Below the basal plane, which is identified automatically using point correspondences of the initial triangulations of the anatomical model, the fiber elevation angle $\alpha$, i.e. their angle with respect to the short axis plane, varies linearly across the myocardium, e.g., from −70 on the epicardium to +70 on the endocardium (values that can be defined by the user). Similarly, the sheet direction, which is defined by the angle $\beta$ with respect to the outward transmural axis, varies transmurally, e.g., from +45 on the epicardium to −45 on the endocardium (values that can be defined by the user). $\alpha$ and $\beta$ are computed for each point of the volumetric bi-ventricular myocardium mesh between the apex and basal plane based on the geodesic distance to the endocardia and epicardia identified by the facet tags: $\alpha=(d_{epi}\alpha_{endo}+d_{endo}\alpha_{epi})/(d_{endo}+d_{epi})$, where $d_{epi}$, $d_{endo}$, $\alpha_{epi}$, and $\alpha_{endo}$ are the distances and angles at the endocardium and epicardium, respectively. The fiber and sheet orientations are then fixed around each valve. In particular, fibers are longitudinal around the aortic valve and tangential around the mitral, tricuspid, and pulmonary valves, and sheet normals are oriented towards the barycenter of the valves. The local orthonormal basis is then interpolated from the basal plane to the valve, first by following the myocardium surface, then throughout the myocardium thickness. Additional details regarding generating the patient-specific anatomical heart model are described in U.S. Published Patent Application No. 2013/0197881 and U.S. Published Patent Application No. 2015/0042464, which are incorporated herein in their entirety by reference. In another embodiment, the fibers are directly measured in-vivo, in the patient, using MRI diffusion tensor imaging. In another embodiment, an atlas of cardiac fibers could be employed. FIG. 3 illustrates exemplary results of generating a patient-specific anatomical heart model. As illustrated in FIG. 3, image 300 shows segmentation results for segmenting the left and right ventricles in a medical image, image 310 shows the LV and RV fused into a single volumetric mesh, and image 320 shows the model of fiber orientation added to the volumetric mesh.

Once the patient-specific anatomical model 212 is generated from the medical image data of the patient, the patient-specific computational heart model is generated by determining patient-specific parameters for the cardiac electrophysiology model 222, cardiac biomechanics model 224, and cardiac hemodynamics model 226, using the patient-specific anatomical model 212 as input. The present disclosure will first discuss techniques for estimating patient-specific parameters for each of these models of cardiac function quantifying uncertainties for these parameters and then discuss a methodology for estimating patient-specific parameters and their uncertainties for at least one of these models of cardiac function. Although various models are discussed to simulate cardiac electrophysiology, cardiac hemodynamics, and cardiac biomechanics, the methodology described herein for calculating model parameters and their uncertainties is not limited to any particular physics, model or parameterization.

The first biophysical phenomenon that needs to be simulated is the cardiac electrophysiology (222), as it commands the cardiac contraction. According to an exemplary embodiment, the cardiac electrophysiology model 222 can compute action potentials over a time period at each of the nodes of the patient-specific anatomical model using a Lattice-Boltzmann method for Electrophysiology method (LBM-EP). A Mitchell-Schaeffer cellular model can be employed as a tradeoff between model fidelity and complexity. Patient-specific parameters of the cardiac electrophysiological model, such as an electrical diffusivity and an action potential duration at each of the nodes of the patient-specific anatomical model, can be estimated using an inverse problem method based on measured electrophysiology data of the patient. For example, the parameters of the cardiac electrophysiology model can be personalized using ECG measurements, invasive endocardial mappings, or body surface mappings of the patient. Additional details regarding the cardiac electrophysiology model and estimating patient-specific parameters of the cardiac electrophysiology model are described in U.S. Published Patent Application No. 2013/0226542 and U.S. Published Patent Application No. 2015/0042646, which are incorporated herein in their entirety by reference.

The cardiac hemodynamics model 226 can compute cardiac blood flow and pressure over a period of time using a lumped model of intra-ventricular pressure that varies according to models of arterial compliance and atrial contraction. A 3-element Windkessel (WK) model can be used as a model of arterial compliance. The cardiac hemodynamics model can be personalized by estimating patient-specific arterial compliance parameters (e.g., patient-specific parameters of the WK model of arterial compliance) from flow and pressure data of the patient measured from medical images (e.g., Doppler Ultrasound or 2D/4D PC-MRI), cuff pressure measurements, or invasive pressure catheter measurements. Additional details regarding the cardiac hemodynamics model and estimating patient-specific parameters of the cardiac hemodynamics model are described in U.S. Published Patent Application No. 2013/0197881, which is incorporated herein in its entirety by reference.

The cardiac biomechanics model 224 simulates movement of the heart chambers over a time period based on the simulated electrophysiology by the cardiac electrophysiology model 222 and the simulated blood flow and pressure by the cardiac hemodynamics model 226. The cardiac biomechanics model 224 can compute the movement of the heart using the finite element method to solve the dynamics equation $M\ddot{u}+C\dot{u}+Ku=f_a+f_p+f_b$. $\ddot{u}$, $\dot{u}$, and u denote nodal accelerations, velocities, and displacements, respectively. M, K, and C are the mass, stiffness, and Rayleigh damping matrices, respectively. Pressure force $f_p$ is calculated from the cardiac hemodynamics model. The active stress $f_a$ is generated by the electrophysiology myocytes and is computed using a phenomenological model of myocyte contraction, which is mainly governed by the maximum active stress parameter $\sigma_0$. Boundary conditions $f_b$ capture heart attachment at the valve plane through springs and pericardium constraints. The orthotropic Holzapfel-Ogden (HO) constitutive law can be used, among others, defined by the stress-strain energy:

$$\Psi = \frac{a}{2b}e^{b(I_1-3)} + \sum_{i=f,s}\frac{a_i}{2b_i}\left[e^{b_i(I_{4i}-1)^2}-1\right] + \frac{a_{fs}}{2b_{fs}}\left[e^{b_{fs}I_{8fs}^2}-1\right]. \quad (1)$$

Subscripts f and s denote fiber and sheet directions, $I_1$, $I_{4\{f,s\}}$, and $I_{8fs}$ are invariants of the deformation tensor, and a, b, $a_{\{f,s,fs\}}$, and $b_{\{f,s,fs\}}$ are patient-specific tissue parameters. Equations 1 can be solved according to multiplicative Jacobian energy decomposition (MJED) formulation or the Total Lagrangian Explicit Dynamics (TLED) for efficient computations. The cardiac biomechanics model 224 can be personalized by estimating patient-specific biomechanical tissue parameters (e.g., stiffness and maximum active stress) based on observed heart movement in the medical images of the patient using inverse problem techniques.

According to an advantageous embodiment, patient-specific parameters and corresponding uncertainty values can be estimated for at least one of the cardiac biomechanics model, the cardiac electrophysiology model, or the cardiac hemodynamics model. For example, in a possible implementation, patient-specific parameters for two of these models of cardiac function can be calculated as described above, with patient-specific parameters and corresponding uncertainties estimated for the remaining one of the models of cardiac function using the methodology described below. In other various embodiments, patient-specific parameters and corresponding uncertainty values can be estimated for computation models of other organs (e.g., heart valves, lung motion, liver heat capacity).

The forward model (e.g., the cardiac biomechanics model, cardiac electrophysiology model, cardiac hemodynamics model, or any other computational model of organ function) can be seen as a dynamic system f that is fully determined by a given set of input parameters θ and whose output, also called responses, are denoted $d^c$. The model is deterministic, i.e., for each set of parameters, θ: $f(\theta) \to d^c$ describes a repeatable mapping to the output.

Bayesian calibration is used to infer values of the parameters θ and to quantify their uncertainty based on noisy measurements $d^m$. Therefore, the forward model f can be reformulated as a statistical forward problem, treating the input θ and output $d^c$ as random variables. The goal is to compute the posterior probability density function (pdf) $p(\theta|d^m)$, namely the probability of having a given set of parameters knowing the measured data $d^m$, based on prior knowledge on the model and uncertainty in the measurements. This is intrinsically related to the forward propagation of uncertainty through f, as shown below. Following the Bayes' theorem, the posterior on the model parameters given the data can be written as:

$$p(\theta|d^m) = \frac{p(d^m|\theta)p(\theta)}{p(d^m)} \propto p(d^m|\theta)p(\theta), \quad (2)$$

where $p(d^m|\theta)$ is called the likelihood, describing how well each set of parameters is supported by the data, and $p(\theta)$ is the prior, representing the knowledge of θ independent from $d^m$. The denominator in the middle term of Equation (2) does not vary with θ and thus is not important in the context of this invention. According to a possible implementation, the prior $p(\theta) = \mathcal{U}(\theta^l; \theta^u)$ can be assumed to be uniformly distributed, with $\theta^l$ and $\theta^u$ denoting the lower and upper limits, respectively for the parameter set θ. However, the present invention is not limited to a uniform distribution and other distributions can be used as well. The likelihood can be estimated through forward simulations by rewriting it in terms of the misfit $\varepsilon(d^c, d^m) = d^c - d^m$ between the responses and measurements. The discrepancy between measurements and responses described by ε is due to several factors, including inaccuracy of the model and measurement noise. In an advantageous implementation, both sources of error can be combined and the error can be assumed to be normally distributed according to $\varepsilon \sim \mathcal{U}(0,\Sigma)$. Thus, the likelihood can be expressed as:

$$p(d^m | \theta) = p(\varepsilon(d^c, d^m) | \theta) \propto \exp\left\{-\frac{1}{2}\varepsilon(d^c, d^m)^T \Sigma^{-1} \varepsilon(d^c, d^m)\right\}. \quad (3)$$

Substituting the likelihood on the right hand side of Equation (2) with Equation (3) allows for sampling the desired posterior density of the model parameters given the observed data using the Markov chain Monte Carlo (MCMC) method. Kernel density estimators can be used to transform discrete samples to a continuous pdf, but a multitude of samples is needed. Hence, in order to generate the posterior pdf, a vast number of forward model runs is required during computation of $d^c=f(\theta)$ for the likelihood calculation. This becomes intractable for computationally expensive models, such as the models of cardiac function (cardiac biomechanics model, cardiac electrophysiology model, and cardiac hemodynamics model) of the computational heart model.

According to an advantageous embodiment of the present invention, to overcome this issue and make the problem computationally tractable, a spectral representation $f^* \approx f$ of the forward model can be used. The spectral representation of the forward model can be estimated based on non-intrusive polynomial chaos expansion (PCE), which is used as a surrogate model for MCMC sampling. Through multi-dimensional orthogonal approximations of f, f* is able to capture the forward model's partial differential equations in an efficient way, providing a functional mapping from model input to responses. The PCE f* for an individual response $r \in d^c$ of the model can be written as:

$$r = \Sigma_{p=0}^{\infty} \alpha_p \psi_p(\theta). \quad (4)$$

PCE is commonly approximated by summation from p=0 ... P on the right-hand side of Equation (4), with the total number of spectral components P<<∞. Since uniformly distributed random variables θ are assumed as input parameters, standard Wiener-Askey Legendre-chaos can be applied directly. The coefficients $\alpha=\{\alpha_p | p=0 \ldots P\}$ are obtained using multidimensional integration by a tensor-product of Gausse-Legendre quadrature rules. We set $$\psi_p(\theta) = L_n(\theta) = \frac{1}{2^n} \sum_{k=0}^{n} \binom{n}{k}^2 (\theta-1)^{n-k}(\theta+1)^k$$

in Equation (4), with $L_n$ denoting the $n^{th}$ order Legendre polynomial in the one-dimensional case. Multivariate polynomial basis functions $\psi_p$ can be computed as the tensor products of 1D basis functions. It should be noted that this framework is not limited to standard distributions, such as uniform or Gaussian. Given the PCE approximation of the computationally expensive forward model, the PCE approximation can be used as an efficient surrogate for generating MCMC samples of the posterior of the parameter space. It should be noted that other techniques to find surrogates, like data-driven based (through principal component analysis or proper orthogonal decomposition) or model simplification could be employed as well. Also, if the original forward model is fast enough, it could be used to compute the MCMC samples. A multi-core, multi-computer architecture could be employed to generate the samples.

A robust parameter estimate is computed and its uncertainty is quantified based on repeated MCMC sampling of posterior densities according to uncertainty levels of noise in the measurements or assumptions in the model (both aspects can be encoded into the posterior probability as discussed above). To that end, a multistep algorithm is employed, in which the number of modes $k_i$ in the posterior is estimated using the mean-shift algorithm. Next, initialized with covariance matrices derived from the clustering information and means from the model locations of the mean-shift estimator, a Gaussian mixture model (GMM) with $k_i$ components $G_i$ is fitted to the MCMC samples. These steps (i.e., MCMC sampling using the surrogate model, determining the number of modes using the mean-shift algorithm, and fitting a GMM to the MCMC samples) are repeated n times with varying levels of measurement noise uncertainty yielding n mixture models $G=G_1 \ldots G_n$. The level of measurement noise uncertainty is varied by varying the covariance matrix $\Sigma$ in the likelihood (Equation (3)). The final estimate of the parameter set is then computed by aggregating the set of GMMs and choosing the most likely point from the set of GMMs according to the following robust approach. It should be noted that if the level of noise is known somehow, only one posterior needs to be estimated for the corresponding level of noise, and no aggregation is necessary anymore.

One preferred embodiment aggregates the plurality of posteriors as follows. Consider one particular mixture model $G_i \in G$. For each of the j=1 ... $k_i$ means $\mu_{ij}$ of the mixture components of $G_i$, its support $\omega_{ij}=\Sigma_{k \neq j} \log G_k(\mu_{ij})$ from all $G_k$ is calculated by summation of log-probabilities for $\mu_{ij}$ in each of the other mixture models. This is performed for all of the mixture models. Then, the means $\mu_{ij}$ from all of the mixture models are separated into k* clusters $C=C_1, \ldots, C_{k^*}$ using $\omega_{ij}$-weighted k-means clustering. k* is determined by a voting scheme: it is the number of GMM components $k_i$ that appears most frequently in G. The centroid $\hat{\mu}_l$ of the $\mu_{ij}$ in the cluster with the highest combined support $\hat{\omega}_l = \Sigma_{\mu_{ij} \in C_l} \omega_{ij}$ is selected as the final estimate for the parameter set. This approach for selecting the final estimate for the parameter set increases robustness in the estimate while considering the fact that the exact level of uncertainty in the measurements is unknown, and is still able to capture multi-modal posteriors.

Uncertainty in the parameters is described by confidence regions. Let $\Sigma_{ij}$ be the covariance matrix of the $j^{th}$ mixture component in the $i^{th}$ mixture model $G_i$. It can be assumed that in each cluster $C_l$, all means $\mu_{ij}$ contained within $C_l$ with corresponding $\Sigma_{ij}$ are distorted (through noise) manifestations of the same probability distribution, which is Gaussian and centered at the centroid $\hat{\mu}_l$ with unknown variance $\hat{\Sigma}_l^*$. The covariance matrices $$\hat{\Sigma}_l = \frac{1}{\hat{\omega}_l} \Sigma_{ij, \mu_{ij} \in C_l} \omega_{ij} \Sigma_{ij}$$

are linearly combined to approximate $\hat{\Theta}_l^*$, which is less prone to noise, as compared to using a single $\Sigma_{ij}$. All of the information from the k* clusters can be merged into a final GMM, which fully describes the uncertainty in the parameters and allows for derivation of the confidence regions: $\hat{G} = \Sigma_l^{k^*} \hat{\omega}_l \mathcal{N}(\hat{\mu}_l, \hat{\Sigma}_l)$.

Figure 4:
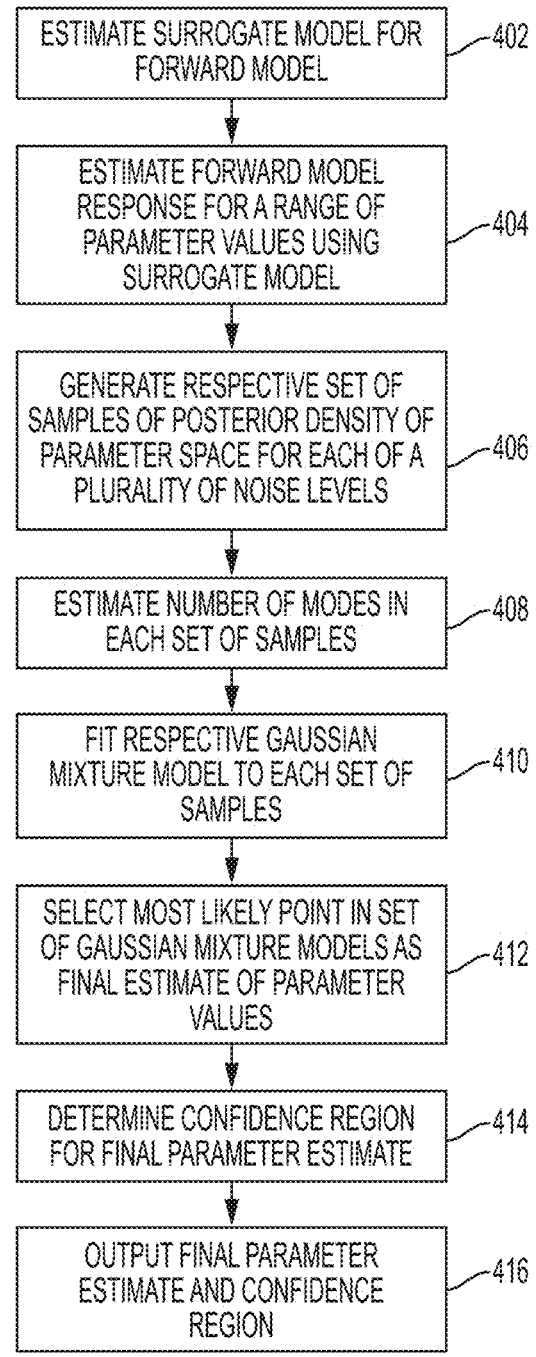
FIG. 4 illustrates a method of estimating patient-specific model parameters and corresponding uncertainty values for a computational model of organ function according to an embodiment of the present invention.

FIG. 4 illustrates a method of estimating patient-specific model parameters and corresponding uncertainty values for a computational model of organ function according to an embodiment of the present invention. The method of FIG. 4 can be used to estimate patient-specific model parameters and corresponding uncertainty values for any computational model of organ function. In the cardiac example of FIGS. 1 and 2, the method of FIG. 4 can be used to estimate patient-specific model parameters and corresponding uncertainty values for at least one of the cardiac biomechanics model, the cardiac electrophysiology model, and the cardiac hemodynamics model of the computational heart model. As illustrated in FIG. 4, at step 402, a surrogate model is estimated for the forward model of organ function if the model is too computationally intensive. As described above the surrogate model is estimated using a PCE approximation of the forward model. The PCE approximation can be low-order or high-order PCE approximation and the coefficients $\alpha_p$ for each response can be estimated from a number of true model evaluations of the forward model. For example, for a PCE approximation of the order p=5, 25 true model evaluations can be used to estimate the coefficients for each response. At step 404, a number of forward model responses (outputs) are estimated using the surrogate model with different parameter values over a range of parameter values.

At step 406, for each of a plurality of noise levels, a respective set of samples of the posterior density of the parameter space is generated. The samples of the posterior density of the parameter space are generated using MCMC sampling based on the forward model responses estimated using the surrogate model. Each MCMC sample corresponds to a particular set of parameter values and a posterior value for that set of parameter values, given the noise level. The posterior value for each set of parameter values for a given noise level is estimated based on the difference between the estimated forward model response for that set of parameters values and the measured data of the patient (e.g., from medical images or clinical measurements of the patient) using Equations (2) and (3). The plurality of noise levels are achieved by varying the covariance matrix in the likelihood calculation of Equation (3).

At step 408, for each of the plurality of noise levels, a number of modes is determined for the respective set of samples of the posterior density of the parameter space. The number of modes for a set of MCMC samples is determined using the mean-shift algorithm. At step 410, for each of the plurality of noise levels, a respective GMM is fit the respective set of samples of the posterior density of the parameter space. The number of mixture components for each GMM is determined to be the number of modes for the corresponding set of MCMC samples. This results in a plurality of GMMs corresponding to the plurality of noise levels, and each GMM represents a probability density function for the parameter space given the corresponding noise level.

At step 412, a most likely point in the set of GMMs is selected as the final estimate of parameter values. In particular, for each GMM, a support value is determined for the mean of each of the mixture components from the other GMMs. The means for all of the mixture models in all of the GMMs are then clustered based on their support values, a cluster with the highest combined support value is determined, and the centroid of the means in the cluster with the highest combine support value is selected. This centroid provides a point in the parameter space, which gives the final estimate of the values for the set of parameters for the computational model. That is, the center of the mode (cluster) corresponds to the estimated model parameters, and the local width of the mode its uncertainty.

At step, 414, a confidence region is estimated for final parameter estimate. In particular, a variance for each cluster is estimated by linearly combining the covariance matrices corresponding to the means in each cluster, and final GMM is estimated based on the centroid of the means in each cluster and the variance estimated for each cluster. The final GMM is a probability density function that is then used to calculate confidence regions around the final parameter estimate.

At step 416, the final parameter estimate and parameter regions are output. For example, the final parameter values and corresponding confidence regions can be output by displaying the parameter values and confidence regions on a display device of computer system.

Figure 5:
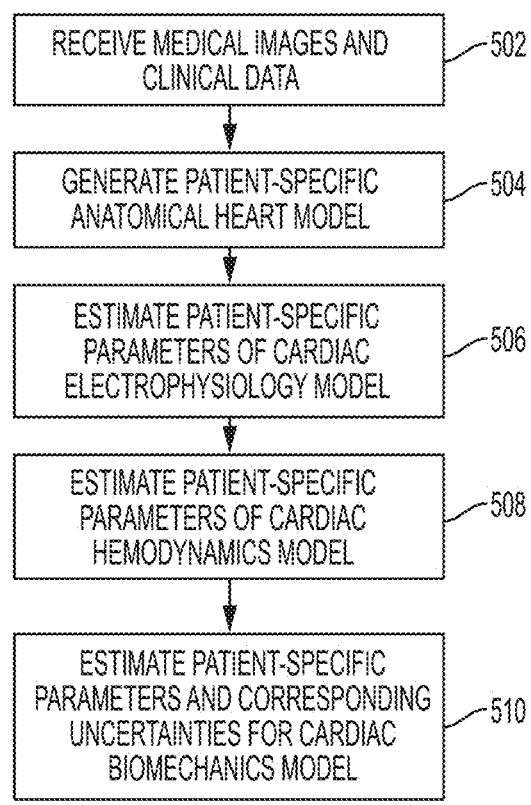
FIG. 5 illustrates a method for estimating patient-specific parameters of a computational heart model according to an embodiment of the present invention.

FIG. 5 illustrates a method for estimating patient-specific parameters of a computational heart model according to an embodiment of the present invention. The method of FIG. 5 can be used to implement step 110 of FIG. 1 and generate a patient-specific computation heart model. Referring to FIG. 5, at step 502, medical images and clinical data of the patient are received. This step is similar to step 100 of FIG. 1. At step 504, the patient-specific anatomical heart model is generated from the medical images of the patient. The patient-specific anatomical heart model is generated as described above in connection with FIG. 2.

At step 506, patient-specific parameters of the cardiac electrophysiology model are estimated. The patient-specific parameters of the cardiac electrophysiology model can be estimated based on ECG measurements, invasive electrocardiography mappings, or body surface potential mappings. For example, the patient-specific parameters of the cardiac electrophysiology model can be estimated using a gradient-free NLS optimizer based on 12-lead ECG data of the patient.

At step 508, patient-specific parameters of the cardiac hemodynamics model are estimated. The patient-specific parameters can be estimated by estimating arterial compliance parameters from flow and pressure data measured from medical images (e.g., Doppler Ultrasound or 2D/4D PC-MRI), cuff blood pressure, or invasive pressure catheter measurements. For example, the arterial compliance parameters can be estimated by estimating the corresponding WK parameters using the simplex method based on invasive pressure measurements and flow data.

At step 510, patient-specific parameters of the cardiac biomechanics model and corresponding uncertainty values are estimated. The patient-specific parameters of the cardiac biomechanics model and the corresponding uncertainty values are estimated using the method of FIG. 4 described above. In an exemplary implementation, the parameters and uncertainty estimation can be performed for global passive and active biomechanical tissue properties, namely the Young modulus E for a linear elastic tissue model and the maximum myocyte contraction $\sigma_0$, thus $\theta=(E,\sigma_0)$. The responses $d^c$ can be features derived from time-series of left ventricular pressure and volume, in particular the minima, maxima, and means of the curves. Pressure data can be acquired through invasive catheterization and volume information can be obtained from cardiac cineMR by segmentation and tracking of the bi-ventricular myocardium. An exemplary implementation that was performed by the present inventors is described herein, but it is to be understood that the present invention is no limited to this specific example. The PCE-based stochastic surrogate model is estimated for the forward cardiac biomechanics model, as described above. In the exemplary implementation, to estimate the coefficients ($\alpha_p$) for each response, 25 true model evaluations were performed on an isotropic grid of size 5×5 within the bounds $\theta^l=(400,100)^T$ and $\theta^u=(800,500)^T$ of the prior model distribution $p(\theta)=\mathcal{U}(\theta^l,\theta^u)$. The mean-shift based posterior analysis was carried out using 15 random noise levels, resulting in 15 GMMs. To estimate the GMMs based on the MCMC samples, the noise level for each response was drawn individually from a uniform distribution $\mathcal{U}(r^l, r^u)$, where $r^l=5$ and $r^u=25$ are the heuristically chosen lower and upper bounds. The response noise levels are the error variances, which can be directly placed into the covariance matrix in Equation (3), which can be assumed to be diagonal. In the exemplary implementation, 50,000 MCMC sample were used for each GMM after discarding the first 10,000 samples as burn-in.

The method of FIG. 5 provides an example in which the parameters of the cardiac electrophysiology and cardiac hemodynamics model are estimated without uncertainty and the method of FIG. 4 is used to estimate the parameters of the cardiac biomechanics model with uncertainty. It is to be understood that, this method can be similarly applied such that the parameters cardiac electrophysiology or the cardiac hemodynamics model can be estimated with uncertainty, while the remaining models are estimated without uncertainty. It is also possible that the parameters for two or all three of these models can be estimated with uncertainty using the method of FIG. 4.

Figure 6:
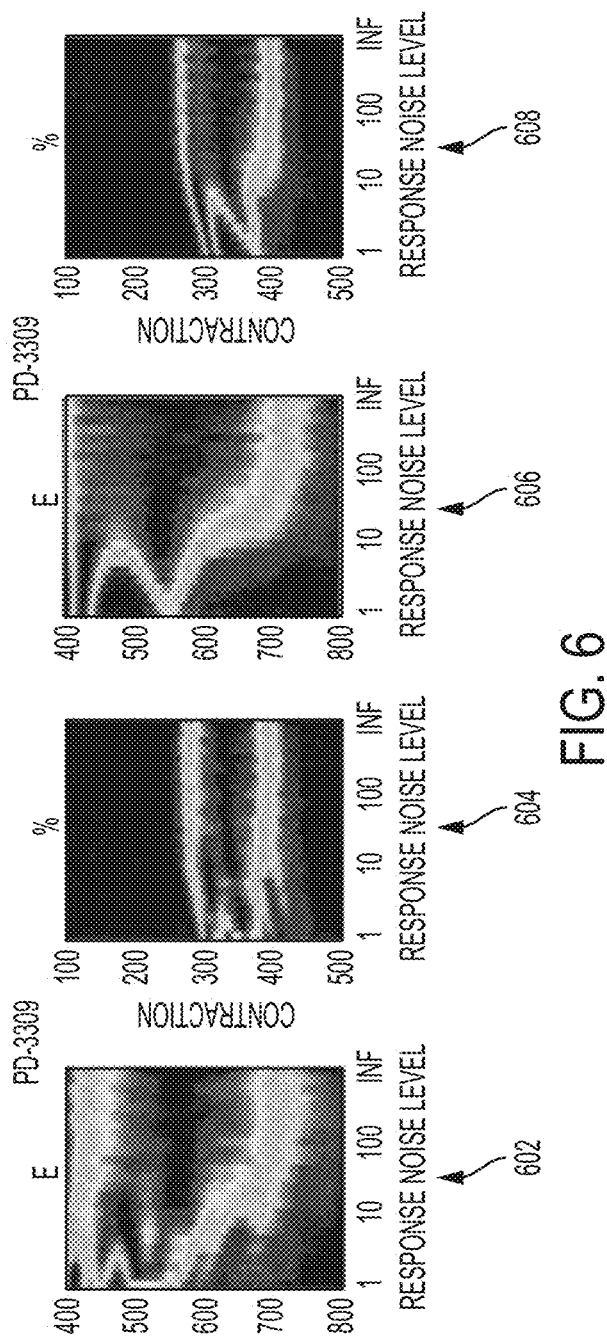
FIG. 6 illustrates posterior densities for passive tissue stiffness and maximum myocyte contraction estimated using high- and low-order polynomial chaos expansion (PCE) approximations of a cardiac biomechanics model.

In order to estimate the posterior pdf of a parameter space, embodiments of the present invention rely on a stochastic surrogate of the forward model, which is based on polynomial chaos expansion (PCE). Since PCE, as used herein, is only an approximation of the complex dynamics of the forward model, the present inventors have conducted a qualitative experiment, in which estimated posteriors of low-order PCE approximations and high-order PCE approximations of the cardiac biomechanics model are compared under varying response noise levels. FIG. 6 illustrates posterior densities for passive tissue stiffness and maximum myocyte contraction estimated using high- and low-order PCE approximations of the cardiac biomechanics model. Images 602 and 604 show posterior densities for the passive tissue stiffness E and the maximum myocyte contraction $\sigma_0$ computed using a PCE of maximum quadrature order 13 and images 606 and 608 show posterior densities for the passive tissue stiffness E and the maximum myocyte contraction $\sigma_0$ computed using a PCE of maximum quadrature order 5. The low-order PCE approximation (p=5) requires 25 true forward model evaluations to estimate its coefficients. The high-order PCE approximation (p=13) requires 169 true forward model runs based on an isotropic 13×13 grid in parameters space. Due to the significantly larger number of ground truth points, the high-order PCE can be assumed to be a better approximation of the true model. However, as can be seen in FIG. 6, the trends of the posteriors are very similar, suggesting that the low-order PCE is a sufficient approximation of the high-order PCE, which is closer to the true model by construction.

Figure 7:
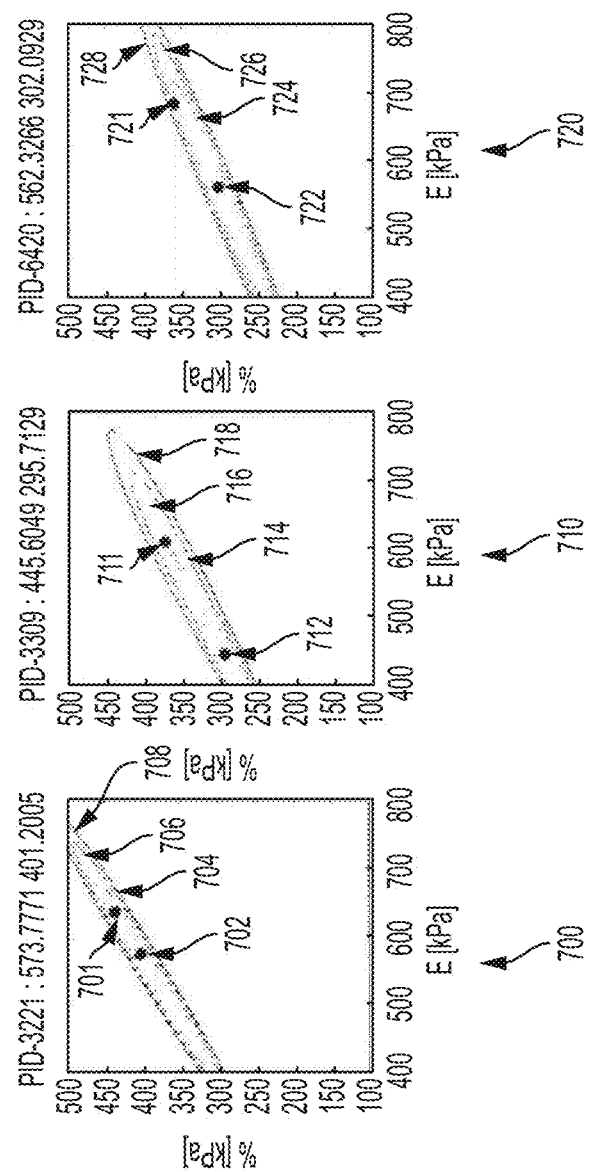
FIG. 7 illustrates a comparison of parameter values for a cardiac biomechanics model estimated using the method of FIG. 4 and using an non-linear least square-based inverse estimation framework.

FIG. 7 illustrates a comparison of parameter values for the cardiac biomechanics model estimated using the method of FIG. 4 and using an NLS-based inverse estimation framework. As shown in FIG. 7, images 700, 710, and 720 show parameter estimation results for three example datasets. Image 700 shows the parameter estimate 702, 80% confidence region 704, 95% confidence region 706, and 99% confidence region 708 estimated using the method of FIG. 4, as well as the NLS estimate 701. Image 710 shows the parameter estimate 712, 80% confidence region 714, 95% confidence region 716, and 99% confidence region 718 estimated using the method of FIG. 4, as well as the NLS estimate 711. Image 720 shows the parameter estimate 722, 80% confidence region 724, 95% confidence region 726, and 99% confidence region 728 estimated using the method of FIG. 4, as well as the NLS estimate 721.

The computed parameters and their uncertainty are displayed to the user. Uncertainty can be displayed by a number, or through color coding (e.g. green for highly confident estimates, yellow, and red for low confidence). The forward model can also be run for various parameters varying within their confidence interval, thus propagation the uncertainty on the model output. If a therapy simulation is performed, the uncertainty can be propagated in a similar way to the therapy prediction, and a color code can be displayed to the user (along with the absolute uncertainty value).

Embodiments of the present invention provide a system and methods for inverse uncertainty quantification and robust parameter estimation for computational models of organ function based on noisy measurements. Through the use of polynomial chaos expansion approximation as a surrogate for the forward model, embodiments of the present invention are able to achieve overall computation times in the same order as existing parameter estimation approaches, which typically yield a single parameter estimate only. Furthermore, the framework described above provides an answer to the question of whether a unique solution exists by estimation the complete probability density of the parameters, which can use useful patient classification and decision making applications.

The framework described above is independent from a particular model or model parameterization. Embodiments of the present invention can be applied for parameter estimation and inverse uncertainty quantification of other forward models than those described herein. For example, embodiments of the present invention can be similarly applied to more complex or regional models of active and physiological or hemodynamic forward models (also jointly), when appropriate clinical measurements are available. Embodiments of the present invention can also be applied to computational models for other organs, such as the lungs, liver, etc. All kinds of clinical measurements that can be computed (simulated) from the forward model can be used in the Bayesian inference process, for example, in order to decrease the uncertainty in the estimated parameters when additional data is available.

Embodiments of the present invention described above utilize a simplified model of measurement noise. If more information of the measurement system (e.g., derived from the imaging device or the invasive pressure catheter) is available, more realistic noise models can be applied. Embodiments of the present invention described above, combine all sources of uncertainty (measurement noise, model assumptions, etc.) into one error term. It is also possible that various independent sources of uncertainty can be incorporated into the framework and the effect of each independent source on the estimated parameters and uncertainty can be evaluated individually.

Figure 8:
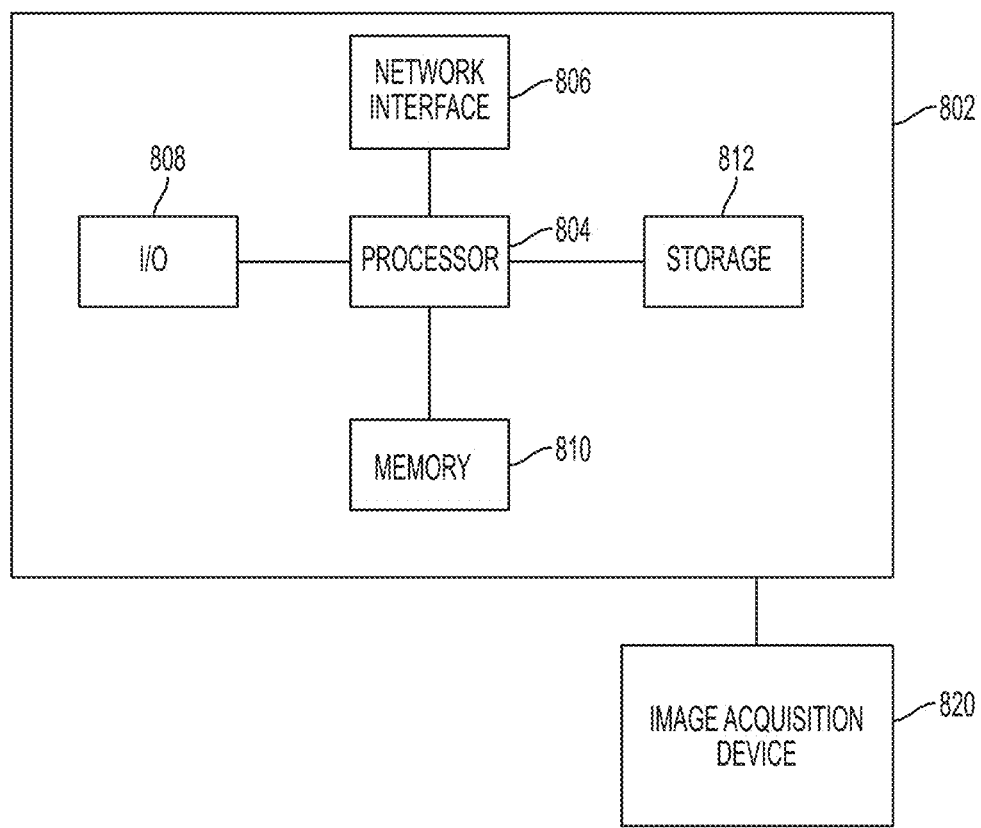
FIG. 8 is a high-level block diagram of a computer capable of implementing the present invention.

The above-described methods for estimating patient-specific parameters and corresponding uncertainty values of a computational model of organ function, patient-specific simulation of cardiac function, and generating a patient-specific computational model of the heart can be implemented on a computer using well-known computer processors, memory units, storage devices, computer software, and other components. A high-level block diagram of such a computer is illustrated in FIG. 8. Computer 802 contains a processor 804, which controls the overall operation of the computer 802 by executing computer program instructions which define such operation. The computer program instructions may be stored in a storage device 812 (e.g., magnetic disk) and loaded into memory 810 when execution of the computer program instructions is desired. Thus, the steps of the methods of FIGS. 1, 2, 4, and 5 may be defined by the computer program instructions stored in the memory 810 and/or storage 812 and controlled by the processor 804 executing the computer program instructions. An image acquisition device 820, such as an MR scanning device, Ultrasound device, etc., can be connected to the computer 802 to input image data to the computer 802. It is possible to implement the image acquisition device 820 and the computer 802 as one device. It is also possible that the image acquisition device 820 and the computer 802 communicate wirelessly through a network. The computer 802 also includes one or more network interfaces 806 for communicating with other devices via a network. The computer 802 also includes other input/output devices 808 that enable user interaction with the computer 802 (e.g., display, keyboard, mouse, speakers, buttons, etc.). Such input/output devices 808 may be used in conjunction with a set of computer programs as an annotation tool to annotate volumes received from the image acquisition device 820. One skilled in the art will recognize that an implementation of an actual computer could contain other components as well, and that FIG. 8 is a high level representation of some of the components of such a computer for illustrative purposes. For example, embodiments of the present invention may be implemented using multi-core architectures, multicomputer architecture, or a cloud based infrastructure, in addition to the computer system described in FIG. 8.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for generating a patient-specific computational model of organ function having patient-specific tissue parameters and corresponding uncertainty values, comprising:
    estimating a plurality of forward model responses for the computational model of organ function corresponding to a plurality of parameter values for tissue parameters of the computational model of organ function;
    generating, for each of a plurality of noise levels, a respective set of samples of a posterior density of a parameter space of the tissue parameters of the computational model of organ function based on the estimated plurality of forward model responses and patient-specific measurements of organ function;
    fitting Gaussian mixture model (GMM) to the respective set of samples for each of the plurality of noise levels based on a number of modes in the respective set of samples, resulting in a plurality of GMMs each corresponding to one of the plurality of noise levels;
    selecting a most likely point from the plurality of GMMs as an estimate of the patient-specific tissue parameters of the computational model of organ function; and
    determining a confidence region for the estimate of the patient-specific tissue parameters based on the plurality of GMMs.

2. The method of claim 1, wherein estimating a plurality of forward model responses for the computational model of organ function corresponding to a plurality of parameter values for tissue parameters of the computational model of organ function comprises:
    estimating a surrogate model for the computational model of organ function; and
    estimating the plurality of forward model responses for the computational model of organ function corresponding to the plurality of parameter values for tissue parameters of the computational model of organ function using the surrogate model.

3. The method of claim 2, wherein estimating a surrogate model for the computational model of organ function comprises:
    estimating a polynomial chaos expansion (PCE) approximation of the computational model of organ function.

4. The method of claim 1, wherein fitting a Gaussian mixture model (GMM) to the respective set of samples for each of the plurality of noise levels based on a number of modes in the respective set of samples comprises:
    determining the number of modes for each respective set of samples.

5. The method of claim 4, wherein determining the number of modes for each respective set of samples comprises:
    determining the number of modes for each respective set of samples using a mean-shift algorithm.

6. The method of claim 1, wherein fitting a Gaussian mixture model (GMM) to the respective set of samples for each of the plurality of noise levels based on a number of modes in the respective set of samples, resulting in a plurality of GMMs each corresponding to one of the plurality of noise levels comprises:
    for each respective set of samples, fitting the Gaussian mixture model to have a number of mixture components corresponding the number of modes in the respective set of samples.

7. The method of claim 6, wherein selecting a most likely point from the plurality of GMMs as an estimate of the patient-specific tissue parameters of the computational model of organ function comprises:
    for each of the plurality of GMMs, calculating, for each of the mixture components of the GMM, a support value for a respective means of each mixture component based on other ones of the plurality of GMMs;
    clustering the means of each mixture component of each of the plurality of GMMs based on the respective support values calculated for each of the means;
    identifying a cluster having a highest combined support value of all of the means in that cluster; and
    selecting a centroid of the cluster having the highest combined support value as the estimate of the patient-specific tissue parameters.

8. The method of claim 7, wherein determining a confidence region for the estimate of the patient-specific tissue parameters based on the plurality of GMMs comprises:
    estimating a variance of each of a plurality of clusters resulting from clustering the means of each mixture component of each of the plurality of GMMs by linearly combining covariance matrices of the means included in each cluster;
    estimating a final GMM based on a centroid of the means included in each cluster and the variance estimated for each cluster; and
    determining the confidence region using the final GMM.

9. The method of claim 1, further comprising:
displaying a visualization of the estimated patient-specific parameters and their uncertainty based on the confidence region.

10. The method of claim 1, further comprising:
performing a simulation of organ function using the computational model of organ function based on the estimated patient-specific tissue parameters and the confidence region.

11. The method of claim 1, further comprising:
performing multiple simulations of organ function with varying patient-specific tissue parameters within the confidence region; and
displaying a visualization of possible simulations outcomes for the computational models of organ function based on the multiple simulations.

12. The method of claim 1, wherein the computational model of organ function is one of a computational heart model, a computational heart valve model, a computation model of liver heat capacity, or a computational model of lung movement.

13. The method of claim 1, wherein the computational model of organ function comprises at least one of a cardiac biomechanics model, a cardiac electrophysiology model, or a cardiac hemodynamics model.

14. A method for patient-specific cardiac therapy planning, comprising:
generating a patient-specific anatomical heart model from medical image data of a patient;
generating a patient-specific computational heart model based on the patient-specific anatomical heart model and patient-specific clinical data, wherein generating the patient-specific computational heart model comprises:
estimating patient-specific parameters and corresponding uncertainty values for at least a subset of parameters of the patient-specific computational heart model by:
estimating a plurality of forward model responses for a forward model of cardiac function in the computational heart model corresponding to a plurality of forward model parameter values,
generating, for each of a plurality of noise levels, a respective set of samples of a posterior density of a parameter space of the forward model parameters based on the estimated plurality of forward model responses and patient specific measurements from the medical image data of the patient or the patient-specific clinical data,
fitting a Gaussian mixture model (GMM) to the respective set of samples for each of the plurality of noise levels based on a number of modes in the respective set of samples, resulting in a plurality of GMMs each corresponding to one of the plurality of noise levels;
selecting a most likely point from the plurality of GMMs as an estimate of the patient-specific parameters, and
determining a confidence region for the estimate of the patient-specific parameters based on the plurality of GMMs; and
simulating cardiac function for the patient using the patient-specific computational heart model.

15. The method of claim 10, wherein estimating a plurality of forward model responses for a forward model of cardiac function in the computation heart model corresponding to a plurality of forward model parameter values comprises:
estimating a surrogate model for the forward model of cardiac function; and
estimating a plurality of forward model responses for a forward model of cardiac function corresponding to the plurality of forward model parameter values using the surrogate model.

16. The method of claim 15, wherein estimating a surrogate model for the forward model of cardiac function comprises:
estimating a polynomial chaos expansion (PCE) approximation of the forward model of cardiac function.

17. The method of claim 10, wherein fitting a Gaussian mixture model (GMM) to the respective set of samples for each of the plurality of noise levels based on a number of modes in the respective set of samples comprises:
determining the number of modes for each respective set of samples.

18. The method of claim 10, wherein fitting a Gaussian mixture model (GMM) to the respective set of samples for each of the plurality of noise levels based on a number of modes in the respective set of samples, resulting in a plurality of GMMs each corresponding to one of the plurality of noise levels comprises:
for each respective set of samples, fitting the Gaussian mixture model to have a number of mixture components corresponding the number of modes in the respective set of samples.

19. The method of claim 18, wherein selecting a most likely point from the plurality of GMMs as an estimate of the patient-specific parameters comprises:
for each of the plurality of GMMs, calculating, for each of the mixture components of the GMM, a support value for a respective means of each mixture component based on other ones of the plurality of GMMs;
clustering the means of each mixture component of each of the plurality of GMMs based on the respective support values calculated for each of the means;
identifying a cluster having a highest combined support value of all of the means in that cluster; and
selecting a centroid of the cluster having the highest combined support value as an estimate of the forward model parameters.

20. The method of claim 19, wherein determining a confidence region for the estimate of the forward model parameters based on the plurality of GMMs comprises:
estimating a variance of each of a plurality of clusters resulting from clustering the means of each mixture component of each of the plurality of GMMs by linearly combining covariance matrices of the means included in each cluster;
estimating a final GMM based on a centroid of the means included in each cluster and the variance estimated for each cluster; and
determining the confidence region using the final GMM.

21. The method of claim 10, wherein estimating patient-specific parameters and corresponding uncertainty values for at least a subset of parameters of the patient-specific computational heart model comprises:
estimating patient-specific parameters and corresponding uncertainty values for at least one of a cardiac biomechanics model, a cardiac electrophysiology model, or a cardiac hemodynamics model.

22. The method of claim 10, wherein estimating patient-specific parameters and corresponding uncertainty values for at least a subset of parameters of the patient-specific computational heart model comprises:

estimating patient-specific tissue parameters and corresponding uncertainties for a cardiac biomechanics model.

23. The method of claim 22, wherein estimating patient-specific tissue parameters and corresponding uncertainties for a cardiac biomechanics model comprises:

estimating Young's modulus and maximum myocyte contraction and corresponding uncertainty values for each of a plurality of points in the patient-specific anatomical model.

24. The method of claim 10, wherein simulating cardiac function for the patient using the patient-specific computational heart model comprises:

performing multiple simulations of a cardiac therapy using the computational heart model with varying values for the subset of parameters within based on the uncertainties estimated for the subset of parameters.

25. The method of claim 24, further comprising:

displaying a visualization of possible cardiac therapy outcomes based on the multiple simulations of the cardiac therapy.

26. An apparatus for generating a patient-specific computational model of organ function having patient-specific tissue parameters and corresponding uncertainty values, comprising:

a processor; and a memory storing computer program instructions, which when executed by the processor cause the processor to perform operations comprising:

estimating a plurality of forward model responses for the computational model of organ function corresponding to a plurality of parameter values for tissue parameters of the computational model of organ function;

generating, for each of a plurality of noise levels, a respective set of samples of a posterior density of a parameter space of the tissue parameters of the computational model of organ function based on the estimated plurality of forward model responses and patient-specific measurements of organ function;

fitting a Gaussian mixture model (GMM) to the respective set of samples for each of the plurality of noise levels based on a number of modes in the respective set of samples, resulting in a plurality of GMMs each corresponding to one of the plurality of noise levels;

selecting a most likely point from the plurality of GMMs as an estimate of the patient-specific tissue parameters of the computational model of organ function; and determining a confidence region for the estimate of the patient-specific tissue parameters based on the plurality of GMMs.

27. The apparatus of claim 26, wherein estimating a plurality of forward model responses for the computational model of organ function corresponding to a plurality of parameter values for tissue parameters of the computational model of organ function comprises:

estimating a surrogate model for the computational model of organ function; and estimating the plurality of forward model responses for the computational model of organ function corresponding to the plurality of parameter values for tissue parameters of the computational model of organ function using the surrogate model.

28. The apparatus of claim 26, wherein fitting a Gaussian mixture model (GMM) to the respective set of samples for each of the plurality of noise levels based on a number of modes in the respective set of samples comprises:

determining the number of modes for each respective set of samples.

29. The apparatus of claim 26, wherein the operations further comprise:

displaying a visualization of the estimated patient-specific parameters and their uncertainty based on the confidence region.

30. The apparatus of claim 26, wherein the operations further comprise:

performing a simulation of organ function using the computational model of organ function based on the estimated patient-specific tissue parameters and the confidence region.

31. The apparatus of claim 26, wherein the operations further comprise:

performing multiple simulations of organ function with varying patient-specific tissue parameters within the confidence region; and displaying a visualization of possible simulations outcomes for the computational models of organ function based on the multiple simulations.

32. An apparatus for patient-specific cardiac therapy planning, comprising:

a processor; and a memory storing computer program instructions, which when executed by the processor cause the processor to perform operations comprising:

generating a patient-specific anatomical heart model from medical image data of a patient;

generating a patient-specific computational heart model based on the patient-specific anatomical heart model and patient-specific clinical data, wherein generating the patient-specific computational heart model comprises:

estimating patient-specific parameters and corresponding uncertainty values for at least a subset of parameters of the patient-specific computational heart model by:

estimating a plurality of forward model responses for a forward model of cardiac function in the computational heart model corresponding to a plurality of forward model parameter values, generating, for each of a plurality of noise levels, a respective set of samples of a posterior density of a parameter space of the forward model parameters based on the estimated plurality of forward model responses and patient specific measurements from the medical image data of the patient or the patient-specific clinical data, fitting a Gaussian mixture model (GMM) to the respective set of samples for each of the plurality of noise levels based on a number of modes in the respective set of samples, resulting in a plurality of GMMs each corresponding to one of the plurality of noise levels;

selecting a most likely point from the plurality of GMMs as an estimate of the patient-specific parameters, and determining a confidence region for the estimate of the forward model parameter values based on the plurality of GMMs; and simulating cardiac function for the patient using the patient-specific computational heart model.

33. The apparatus of claim 32, wherein estimating a plurality of forward model responses for a forward model of cardiac function in the computation heart model corresponding to a plurality of forward model parameter values comprises:
    estimating a surrogate model for the forward model of cardiac function; and
    estimating a plurality of forward model responses for a forward model of cardiac function corresponding to the plurality of forward model parameter values using the surrogate model.

34. The apparatus of claim 32, wherein fitting a Gaussian mixture model (GMM) to the respective set of samples for each of the plurality of noise levels based on a number of modes in the respective set of samples comprises:
    determining the number of modes for each respective set of samples.

35. The apparatus of claim 32, wherein estimating patient-specific parameters and corresponding uncertainty values for at least a subset of parameters of the patient-specific computational heart model comprises:
    estimating patient-specific parameters and corresponding uncertainty values for at least one of a cardiac biomechanics model, a cardiac electrophysiology model, or a cardiac hemodynamics model.

36. The apparatus of claim 32, wherein simulating cardiac function for the patient using the patient-specific computational heart model comprises:
    performing multiple simulations of a cardiac therapy using the computational heart model with varying values for the subset of parameters within based on the uncertainties estimated for the subset of parameters.

37. The apparatus of claim 35, wherein the operations further comprise:
    displaying a visualization of possible cardiac therapy outcomes based on the multiple simulations of the cardiac therapy.

38. A non-transitory computer readable medium storing computer program instructions for generating a patient-specific computational model of organ function having patient-specific tissue parameters and corresponding uncertainty values, which when executed by a processor cause the processor to perform operations comprising:
    estimating a plurality of forward model responses for the computational model of organ function corresponding to a plurality of parameter values for tissue parameters of the computational model of organ function;
    generating, for each of a plurality of noise levels, a respective set of samples of a posterior density of a parameter space of the tissue parameters of the computational model of organ function based on the estimated plurality of forward model responses and patient-specific measurements of organ function;
    fitting a Gaussian mixture model (GMM) to the respective set of samples for each of the plurality of noise levels based on a number of modes in the respective set of samples, resulting in a plurality of GMMs each corresponding to one of the plurality of noise levels;
    selecting a most likely point from the plurality of GMMs as an estimate of the patient-specific tissue parameters of the computational model of organ function; and
    determining a confidence region for the estimate of the patient-specific tissue parameters based on the plurality of GMMs.

39. The non-transitory computer readable medium of claim 38, wherein estimating a plurality of forward model responses for the computational model of organ function corresponding to a plurality of parameter values for tissue parameters of the computational model of organ function comprises:
    estimating a surrogate model for the computational model of organ function; and
    estimating the plurality of forward model responses for the computational model of organ function corresponding to the plurality of parameter values for tissue parameters of the computational model of organ function using the surrogate model.

40. The non-transitory computer readable medium of claim 38, wherein fitting a Gaussian mixture model (GMM) to the respective set of samples for each of the plurality of noise levels based on a number of modes in the respective set of samples comprises:
    determining the number of modes for each respective set of samples.

41. The non-transitory computer readable medium of claim 38, wherein the operations further comprise:
    displaying a visualization of the estimated patient-specific parameters and their uncertainty based on the confidence region.

42. The non-transitory computer readable medium of claim 38, wherein the operations further comprise:
    performing a simulation of organ function using the computational model of organ function based on the estimated patient-specific tissue parameters and the confidence region.

43. The non-transitory computer readable medium of claim 38, wherein the operations further comprise:
    performing multiple simulations of organ function with varying patient-specific tissue parameters within the confidence region; and
    displaying a visualization of possible simulations outcomes for the computational models of organ function based on the multiple simulations.

44. A non-transitory computer readable medium storing computer program instructions for patient-specific cardiac therapy planning, the computer program instructions when executed by a processor cause the processor to perform operations comprising:
    generating a patient-specific anatomical heart model from medical image data of a patient;
    generating a patient-specific computational heart model based on the patient-specific anatomical heart model and patient-specific clinical data, wherein generating the patient-specific computational heart model comprises:
        estimating patient-specific parameters and corresponding uncertainty values for at least a subset of parameters of the patient-specific computational heart model by:
            estimating a plurality of forward model responses for a forward model of cardiac function in the computational heart model corresponding to a plurality of forward model parameter values,
            generating, for each of a plurality of noise levels, a respective set of samples of a posterior density of a parameter space of the forward model parameters based on the estimated plurality of forward model responses and patient specific measurements from the medical image data of the patient or the patient-specific clinical data,
            fitting a Gaussian mixture model (GMM) to the respective set of samples for each of the plurality of noise levels based on a number of modes in the respective set of samples, resulting in a plurality of GMMs each corresponding to one of the plurality of noise levels;
selecting a most likely point from the plurality of GMMs as an estimate of the patient-specific parameters, and
determining a confidence region for the estimate of the patient-specific parameters based on the plurality of GMMs; and
simulating cardiac function for the patient using the patient-specific computational heart model.

45. The non-transitory computer readable medium of claim 44, wherein estimating a plurality of forward model responses for a forward model of cardiac function in the computation heart model corresponding to a plurality of forward model parameter values comprises:
estimating a surrogate model for the forward model of cardiac function; and
estimating a plurality of forward model responses for a forward model of cardiac function corresponding to the plurality of forward model parameter values using the surrogate model.

46. The non-transitory computer readable medium of claim 44, wherein fitting a Gaussian mixture model (GMM) to the respective set of samples for each of the plurality of noise levels based on a number of modes in the respective set of samples comprises:
determining the number of modes for each respective set of samples.

47. The non-transitory computer readable medium of claim 44, wherein estimating patient-specific parameters and corresponding uncertainty values for at least a subset of parameters of the patient-specific computational heart model comprises:
estimating patient-specific parameters and corresponding uncertainty values for at least one of a cardiac biomechanics model, a cardiac electrophysiology model, or a cardiac hemodynamics model.

48. The non-transitory computer readable medium of claim 44, wherein simulating cardiac function for the patient using the patient-specific computational heart model comprises:
performing multiple simulations of a cardiac therapy using the computational heart model with varying values for the subset of parameters within based on the uncertainties estimated for the subset of parameters.

49. The non-transitory computer readable medium of claim 48, wherein the operations further comprise:
displaying a visualization of possible cardiac therapy outcomes based on the multiple simulations of the cardiac therapy.

50. The method of claim 10, wherein performing a simulation of organ function using the computational model of organ function based on the estimated patient-specific tissue parameters and the confidence region comprises:
simulating organ function in response to a therapy using the computational model of organ function based on the estimated patient-specific tissue parameters and the confidence region; and
calculating one or more simulated parameters based on the simulated organ function in response to the therapy, wherein the one or more simulated parameters provide predictors of the patient response to the therapy.

51. The method of claim 14, wherein simulating cardiac function for the patient using the patient-specific computational heart model comprises:
simulating cardiac function for the patient in response to a cardiac therapy using the patient-specific computational heart model; and
calculating one or more simulated parameters based on the simulated cardiac function in response to the cardiac therapy, wherein the one or more simulated parameters provide predictors of the patient response to the cardiac therapy.

\* \* \* \* \*